US008874212B2

(12) United States Patent
Euzen et al.

(10) Patent No.: US 8,874,212 B2
(45) Date of Patent: Oct. 28, 2014

(54) ACTIVE IMPLANTABLE MEDICAL DEVICE TYPE SUCH AS A PACEMAKER WITH DETECTION OF ANODAL STIMULATION BY ANALYSIS OF A VECTOGRAM

(71) Applicant: Sorin CRM S.A.S., Clamart Cedex (FR)

(72) Inventors: Marie-Anne Euzen, Bievres (FR); Elodie Vincent, Antony (FR); Laurence Graindorge, Thouaré sur Loire (FR)

(73) Assignee: Sorin CRM S.A.S., Clamart Cedex (FR)

( * ) Notice: Subject to any disclaimer, the term of this patent is extended or adjusted under 35 U.S.C. 154(b) by 0 days.

(21) Appl. No.: 14/106,093

(22) Filed: Dec. 13, 2013

(65) Prior Publication Data

US 2014/0172037 A1   Jun. 19, 2014

(30) Foreign Application Priority Data

Dec. 14, 2012   (FR) ..................................... 12 62074

(51) Int. Cl.
*A61N 1/00*   (2006.01)
*A61N 1/365*   (2006.01)
*A61B 5/0452*   (2006.01)
*A61N 1/37*   (2006.01)

(52) U.S. Cl.
CPC .............. *A61N 1/365* (2013.01); *A61B 5/0452* (2013.01); *A61N 1/371* (2013.01)
USPC .......................................................... 607/18

(58) Field of Classification Search
CPC ....... A61N 1/371; A61N 1/362; A61N 1/361; A61N 1/365; A61N 1/368
USPC ........................................................... 607/18
See application file for complete search history.

(56) References Cited

U.S. PATENT DOCUMENTS

| 2008/0071318 | A1 | 3/2008 | Brooke et al. |
| 2009/0030470 | A1 | 1/2009 | Holmstrom et al. |
| 2010/0262204 | A1 | 10/2010 | McCabe et al. |

FOREIGN PATENT DOCUMENTS

| EP | 2 105 843 A1 | 9/2009 |
| EP | 2 324 885 A1 | 5/2011 |
| EP | 2 368 493 A1 | 9/2011 |

OTHER PUBLICATIONS

Search Report for French Patent Application 1262074, dated Apr. 17, 2013, 2 pages.

*Primary Examiner* — Robert N Wieland
(74) *Attorney, Agent, or Firm* — Foley & Lardner LLP

(57) ABSTRACT

A device produces at least two distinct temporal components ($V_{bip}$, $V_{uni}$) from two separate endocardial electrogram EGM signals concurrently collected in the same cavity. A 2D non-temporal characteristic is determined from the variations of one of the temporal components ($V_{uni}$) versus the other ($V_{bip}$). The analysis of this characteristic allows detection of the possible presence of an anodal stimulation, causing a depolarization in a second cavity after stimulation delivered to a first heart chamber, opposite to the first. One possibility is to proceed by observing whether the non-temporal 2D characteristic is included or not within a predetermined domain defined in a coordinate frame corresponding to the space of the two temporal components.

21 Claims, 3 Drawing Sheets

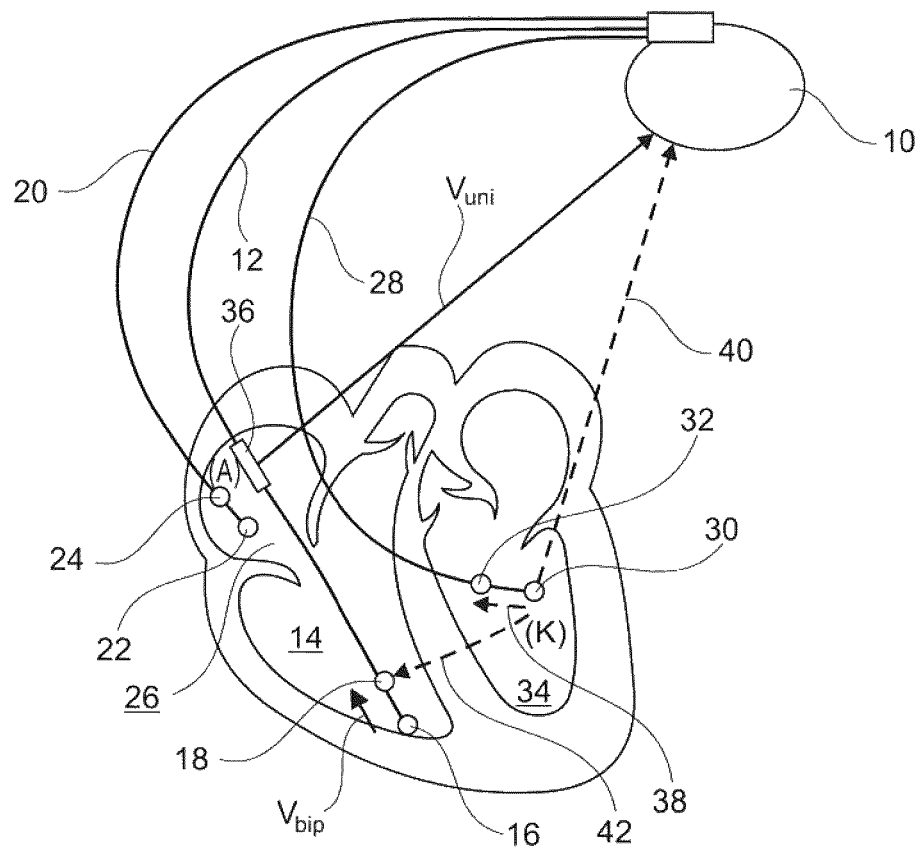
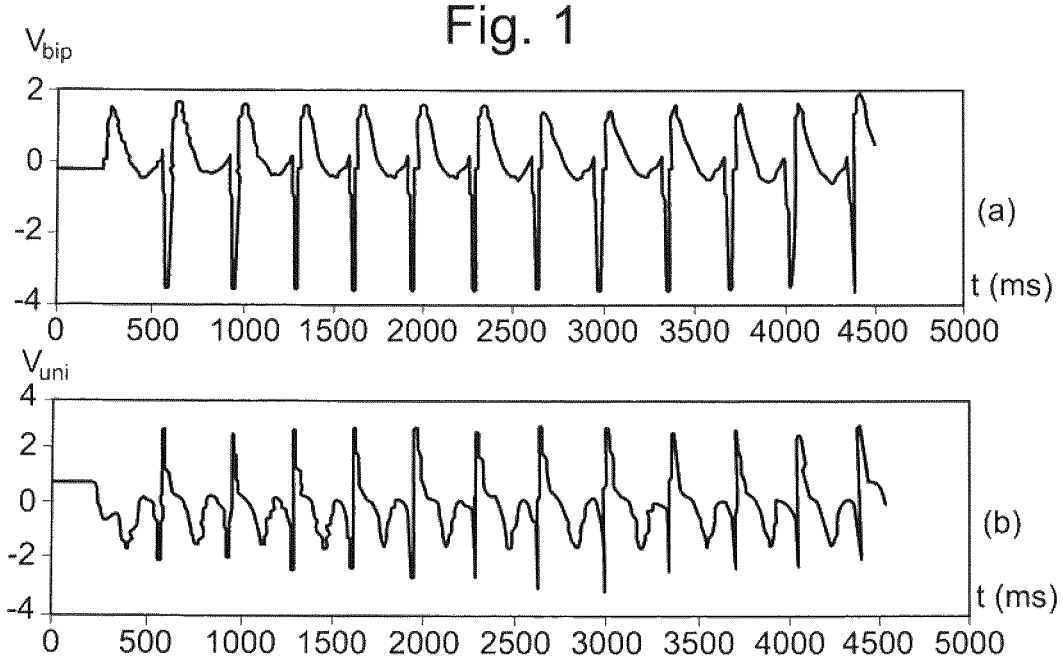
Fig. 2

ACTIVE IMPLANTABLE MEDICAL DEVICE TYPE SUCH AS A PACEMAKER WITH DETECTION OF ANODAL STIMULATION BY ANALYSIS OF A VECTOGRAM

CROSS-REFERENCE TO RELATED APPLICATION

This application claims the benefit of and priority to French Patent Application No. 1262074, filed Dec. 14, 2012, which is incorporated herein by reference in its entirety.

BACKGROUND

The invention relates to "active implantable medical devices" as defined by Directive 90/385/EEC of 20 Jun. 1990 of the Council of the European Communities, specifically implants to continuously monitor heart rhythm and deliver if necessary to the heart electrical pulses for stimulation, resynchronization and/or defibrillation in case of rhythm disorder detected by the device.

Bradycardia pacing involves the controlled delivery of pulses to the atrium and/or to the ventricle (simple or dual chamber devices). In the case of cardiac resynchronization therapy (CRT), stimulation must also be applied in conjunction to the two ventricles (multisite device).

The invention relates more particularly to the detection of "anodic stimulation," which is characterized by a reversal of the cathode and the anode during stimulation, resulting in that the stimulation is not delivered in the required manner and that the depolarization wave induced by this improper stimulation is not as expected, with all the adverse effects that may result.

Certain conditions favor the occurrence of this phenomenon, in particular:

Relatively high stimulation amplitudes, nevertheless close to the stimulation threshold; and An "intercavity stimulation vector" configuration, that is to say, a configuration in which a stimulus is applied in a given cavity (for example the left ventricle) with the anode in a lead implanted in the opposite cavity (for example an electrode of a right ventricular lead).

These conditions typically occur during the execution of a "capture test," which is a test of determining whether stimulation was effective or not by research and analysis of the "evoked wave," that is to say of the depolarization wave induced by stimulation of a cavity. This test should be performed at regular intervals, and can also be made permanently, cycle to cycle. It is intended to regularly adjust the amplitude and/or the width of the stimulation pulses, that is to say, the energy delivered to the stimulation site, depending on the myocardium response to these pulses.

In some cases, detection of the pacing threshold must be made indirectly, with a detection within a cavity which is different than that which is stimulated, for example by stimulation of the sole left ventricle and detection of signals collected in the right ventricle. In such a situation, the cycles with anodic stimulation must be excluded from the analysis of the signal, because they are not representative and therefore cannot be properly discriminated in capturing cycles or non-capturing cycles.

Anodal stimulation also produces deleterious effects in patients undergoing a cardiac resynchronization therapy (CRT), in which a non-zero delay between the two ventricular stimulations (interventricular delay or VVD) is implemented and adjusted to optimize the hemodynamic response of the patient. Under these conditions, anodic stimulation is characterized for example by stimulation of the left ventricle causing a concomitant contraction of the right ventricle, resulting in loss of the VVD. This phenomenon is not uncommon in patients undergoing biventricular pacing; it can be detected and the device may take appropriate measures, such as changing the pacing configuration with switching to another stimulation vector with which there is no anodic stimulation (such as a bipolar vector, an unipolar vector or another interventricular vector by selection of other electrodes of the lead).

Various techniques have been proposed to detect the emergence or presence of an anodic stimulation, for example, as described in U.S. 2009/0030470 A1, U.S. 2010/0262204 A1, U.S. 2008/0071318 A1, U.S. Pat. No. 6,687,545 B1 or WO 2012/071331 A2.

These known detection methods are generally based on the observation that if a stimulus in a given cavity causes an immediate depolarization in the opposite cavity, this reveals the presence of an anodic stimulation, while a late depolarization in this opposite cavity indicates the absence of anodal stimulation.

With these known techniques, the detection is based on the analysis of a single endocardial electrogram signal (EGM signal), which has the disadvantage that the detection entirely depends on the quality of that EGM, which can sometimes be compromised.

SUMMARY

Embodiments of the invention collect and combine two EGMs from the same cavity to reduce the risk of erroneous diagnosis of presence/absence of anodal stimulation due to degraded EGM quality. This technique can use correct EGM quality on one channel to compensate for degraded quality in another channel.

In an exemplary embodiment, the two EGM signals are combined so as to allow a two-dimensional analysis of the "heart loop" or "vectogram" (VGM), which is the representation in a two-dimensional space of one of the two EGM signals (y-vertical axis) versus the other (x-horizontal axis), each beat or significant fraction of beat being then represented by its vectogram in the plane thus defined—and therefore ignoring the temporal dimension.

This "vectogram" (VGM), which is obtained from electrogram signals (EGM) from intracardiac leads should not be confused with a "vectocardiogram" (VCG), which may obtained from electrocardiogram signals (ECG) from external electrodes located on the patient's chest.

The two different EGM channels may be that of a unipolar signal (remote or far-field signal collected between the housing and a distal or proximal electrode of the lead), and that of a bipolar signal (close or near-field signal collected between a distal electrode and a proximal electrode of the same lead).

The analysis of a VGM has been proposed for other purposes, notably by EP 2105843 A1 (Sorin CRM, previously known as ELA Medical) for discriminating between ventricular tachycardia (TV) and supraventricular tachycardia (SVT), by EP 2324885 A1 (Sorin CRM) for the invalidation of a capture test in case of fusion, that is to say, stimulation triggered concomitantly with spontaneous depolarization, or by EP 2368493 A1 (Sorin CRM) for discriminating noise artifacts for the validation or invalidation of the cardiac cycles to be analyzed, in particular for the application of defibrillation therapy or antitachycardia pacing (ATP).

Embodiments of the present application include a device configured to detect anodal stimulation. The device can include a stimulator for delivering electrical stimulation pulses to electrodes implanted in at least one of a heart chamber of a patient. The device can include a lead or leads, and electrodes for collecting endocardial electrogram signals (EGM) representative of depolarization cardiac potentials. The device can detect a depolarization induced in a second cardiac chamber by a stimulation delivered to a first cardiac chamber, opposite the first. The device may further include a circuit for detecting an anodal stimulation. The circuit may be configured to cause a stimulation pulse to be provided to the first cavity during at least one cardiac cycle. The circuit may further be configured to concurrently collect, in the second cavity, at least two distinct EGM signals and to derive at least two respective distinct temporal components (voltage readings for given time periods). The circuit may combine the two components to obtain a non-temporal 2D characteristic representative of the cardiac cycle to be analyzed (e.g., a vectogram where the two axis are voltage-voltage pairs matched or paired by time or series). The circuit can further be configured to determine the presence or absence of anodal stimulation by analysis of non-temporal 2D characteristic.

According to various embodiments:

The device may include a ventricular lead adapted to be implanted in the second cavity and have a distal electrode, a proximal electrode and optionally a defibrillation coil. One of the temporal components may be derived from a bipolar near-field EGM signal collected between the distal electrode and the proximal electrode of the ventricular lead. The other of the temporal components may be derived from a unipolar far-field EGM signal collected between, firstly, the distal electrode, the proximal electrode or the defibrillation coil of the ventricular lead, and, secondly, by a metallic housing of a generator of the device;

Determining the non-temporal 2D characteristic (vectogram) may include determining this characteristic from the variations of the temporal components on a portion of the cardiac cycle to be analyzed. The readings to find the temporal components may be conducted by using a temporal analysis window, open at the instant of delivery of a pacing pulse in the first cavity or shifted relatively to this instant;

Embodiments of the device according to this application may also temporarily shorten the atrioventricular delay of the device during the activation of the detection means of anodal stimulation, so that a spontaneous ventricular contraction occurring after an absence of ventricular depolarization has a better chance of being collected outside of the analysis time window;

The device may be configured to determine a predetermined domain in a reference corresponding to the space of the two temporal components. The device may be configured to determine whether the non-temporal 2D characteristic is included or not in the domain and decide i) the absence of anodal stimulation in the first case and ii) the presence of an anodal stimulation in the second case;

This domain may be a rectangular area, and it may be centered on the point of origin of the coordinate corresponding to the space of the two temporal components;

The non-temporal 2D characteristic may be a sampled 2D characteristic described by a series of successive discrete points, and the topological analysis may analyze the relative position of each point relative to the domain;

The topological analysis may determine that the 2D characteristic is not included in the domain when at least one point on the sampled 2D characteristic is outside the domain, or if at least two points of the sampled 2D characteristic are outside the domain, including at least two consecutive points;

Non-temporal 2D characteristics are determined for a plurality of respective successive cardiac cycles, and the topological analysis may be able to determine the presence of anodic stimulation if at least one of the characteristics thus determined is outside the domain, and the absence of anodal stimulation otherwise;

The device may further be configured to perform a capture test (e.g., adapted to detect the occurrence of a depolarization wave induced in the first cavity or in a cavity opposite by the stimulation of this first cavity); and to inhibit the capture test means upon detection of an anodal stimulation.

A device according to an embodiment of the invention produces at least two distinct temporal components ($V_{bip}$, $V_{uni}$) from two separate endocardial electrogram (EGM) signals (10, 16, 18, 36) concurrently collected in the same cavity (14). A 2D non-temporal characteristic is determined from the variations of one of the temporal components ($V_{uni}$) versus the other ($V_{bip}$). The analysis of this characteristic is used to detect the presence of an anodal stimulation (e.g., causing a depolarization in a second cavity (14) after stimulation (10, 30, 32) delivered to a first heart chamber (34), opposite to the first). In one embodiment the device evaluates whether the non-temporal 2D characteristic is included or not within a predetermined domain (e.g., an area, a two dimensional range, a rectangular bounding box, etc.) defined in a coordinate frame corresponding to the space of the two temporal components.

BRIEF DESCRIPTION OF THE FIGURES

FIG. 1 is an illustration of a bipolar lead implanted at the apex of the right ventricle of the heart.

FIG. 2 illustrates the EGM signals respectively obtained on the bipolar and unipolar ventricular channels of the lead of FIG. 1.

DETAILED DESCRIPTION

Figure 3:
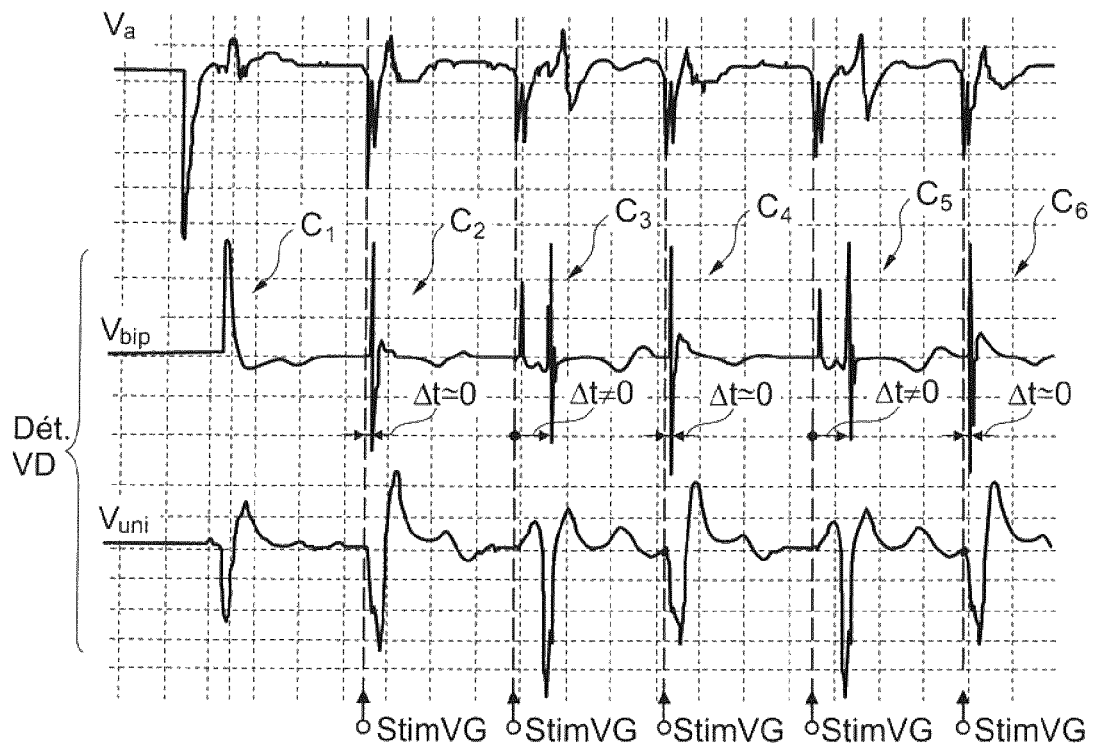
FIG. 3 is an example of EGM signals obtained on a plurality of successive cycles, some of which exhibit a phenomenon of anodal stimulation, and others do not.

Embodiments of the invention may include programming the controlling software of a stimulator, for example, a cardiac pacemaker, resynchronizer and/or defibrillator. The device may include appropriate circuitry for acquiring a signal provided by endocardial leads and/or one or more implanted sensors.

These devices include programmable microprocessor circuitry to receive, format and process electrical signals collected by implantable electrodes. The devices can also deliver stimulation pulses to these electrodes. Program code for the methods described herein may be stored in memory and transmitted, via telemetry software, to another device that will be stored in memory and executed to implement the functions of the invention that are described below. The method of the invention may be conducted using appropriate algorithms executed by a microcontroller or a digital signal processor.

The invention may be applied to implantable devices such as that of the Reply and Paradym product families produced and marketed by Sorin CRM, Clamart, France.

As was mentioned above, the detection technique of the invention includes analyzing the evoked wave following the stimulation of a cavity from electrogram signals (EGM) collected on two separate channels and analyzed in two dimensions. FIG. 1 illustrates a pulse generator 10 associated with a first lead 12 located in the right ventricle 14. The head of the lead comprises two electrodes, namely a distal electrode (tip) 16 and a proximal electrode (ring) 18. An atrial lead 20, provided with distal 22 and proximal 24 sensing electrodes may be placed in the right atrium 26 for the detection of signals in this cavity and for the possible application of an atrial stimulation.

In the case of biventricular pacing (e.g., for restoring synchronization between the two ventricles), the device is provided with a second ventricular lead 28. The second ventricular lead 28 may be disposed in the coronary network and have one or more electrodes 30, 32 disposed in the vicinity of the left ventricle 34. It is thus possible to ensure the simultaneous stimulation, or with a slight controlled temporal delay (interventricular delay VVD) of both the right and left ventricles to restore the synchronization between these two cavities and improve overall patient hemodynamic. The right ventricular lead 12 can also be provided with a coil forming a ventricular defibrillation electrode 36, for also collecting an EGM endocardial signal.

For left ventricular stimulation, it is possible to use a bipolar configuration (between the two electrodes 30 and 32 of the lead 28) or an unipolar configuration (between an electrode 30 or 32 and the housing (can) 10 of the generator). Both corresponding stimulation vectors are referenced 38 and 40 in FIG. 1.

The anodal stimulation phenomenon may appear when the current return is not made on the electrode 32 (in bipolar stimulation) or on the housing of the generator 10 (in unipolar stimulation), but on an electrode in the opposite ventricle, for example on the ring electrode 18 of the right ventricular lead 12 which then forms the anode 42 of the pacing vector (instead of vector 38 or 40, as appropriate), the cathode corresponding to the electrode wherein the stimulation pulse is applied by the generator, in this case the left ventricular tip electrode 30 on the example of FIG. 1. This has the consequence that the depolarization wave corresponding to the pulse applied to the left cavity propagates mainly in the right ventricle, leading to the loss of stimulation in the left cavity and, then, of the resynchronization therapy.

In the case of a capture threshold test, beginning with high stimulation energy, the risk of occurrence of anodal stimulation may be relatively high. The risk then progressively decreases as the amplitude of stimulation is reduced, but the test algorithm has been lured by wrongly interpreting the disappearance of the anodal stimulation as a loss of capture, leading to a misclassification of successive cycles of the test.

An object of the invention is to remedy this confusion between loss of capture and disappearance of the anodal stimulation. An exemplary method described herein advantageously provides a new detection technique for detecting the occurrence of the phenomenon of anodal stimulation to accurately discriminate ventricular cycles having such a phenomenon and exclude them from the analysis performed by the capture test algorithm.

With reference to the example of FIG. 1, the method includes combining two EGMs obtained from the same cavity, in this case from the right ventricle (that is to say of the cavity which is not intended to be stimulated by the application of a pacing pulse to the left ventricle). With continuing reference to the example of FIG. 1, the two EGMs obtained are:

A $V_{bip}$ component derived from a bipolar near-field EGM signal collected between the distal electrode 16 and the proximal electrode 18 of the right ventricular lead 12, and The other $V_{uni}$ component derived from a unipolar far-field EGM signal collected between the defibrillation coil 36 of the right ventricular lead 12 and the metal housing of the generator 10.

Other configurations may be used in varying alternative embodiments. For example, far-field signals (e.g. between one of the electrodes 16 and 18 and the housing 10) and near-field signals from the ventricular cavity would not normally be stimulated (in the absence of anodal stimulation). In many cases the cavity for monitoring will be the right ventricle.

FIG. 2 shows an example of $V_{bip}$ and $V_{uni}$, electrogram plots collected from the ventricular bipolar channel (plot a) and on the ventricular unipolar channel (plot b) of the system of FIG. 1.

FIG. 3 is an example of EGM signals collected with the timing diagrams of the $V_{bip}$ and $V_{uni}$, ventricular EGMs and the atrial EGM signal $V_a$. In addition, StimVG markers indicate the times of application of the left ventricular stimulation. In this figure, six cycles $C_1$ to $C_6$ are visible, the $C_2$ to $C_6$ cycles being cycles collected in the right cavity in the presence of stimulation in the left cavity (and only in the left cavity). These cycles can be for example those collected during a capture test with variable amplitude, for the highest values of the amplitude (about 4.5 V), which as explained above favor the appearance a phenomenon of anodal stimulation.

On the five cycles, the $C_2$, $C_4$ and $C_6$ cycles show a phenomenon of anodal stimulation, with a detected depolarization on the right ventricle virtually concomitant ($\Delta t \approx 0$) with application of the stimulation of the left ventricle. In other words, there is capture in the right cavity of the stimulation that was applied to the left cavity.

By contrast, the $C_3$ and $C_5$ cycles do not exhibit this phenomenon of anodal stimulation: there is a delay ($\Delta t \neq 0$) between the stimulation of the left ventricle and the occurrence of the depolarization wave, naturally led from the left ventricle to the right ventricle and detected on the $V_{bip}$ and $V_{uni}$, EGMs of the right ventricle.

Figure 4A:
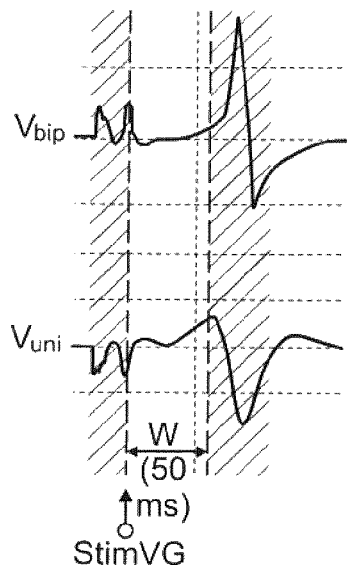
FIGS. 4a and 4b are enlarged views of two isolated cycles, respectively with and without anodal stimulation, and illustrating an analysis window for the detection of this phenomenon.
Figure 4B:
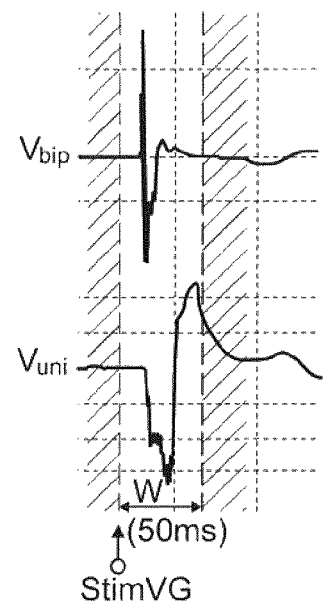

Systems and methods of the present application are configured to identify the cycles wherein the depolarization is due to anodal stimulation by evaluating the components of the signal during the delay time $\Delta t$. This evaluation may be conducted by defining, as shown in FIGS. 4a and 4b, a window of width W, e.g., W=50 ms, the window being counted from the moment StimVG of application of the stimulation pulse. This window is used to notably collect samples of $V_{bip}$ and $V_{uni}$, signals that: i) correspond to a baseline signal in the case of a cycle with capture or of a cycle without capture and ii) correspond to a depolarization in the case of an anodal stimulation.

The length W of the window can be different from the value specified in this example, and the start of the window can optionally be shifted in time relative to the timing of the stimulation. The width W and the starting time of the window may also be parameterized values to allow their adaptation to the individual patient.

Figure 5:
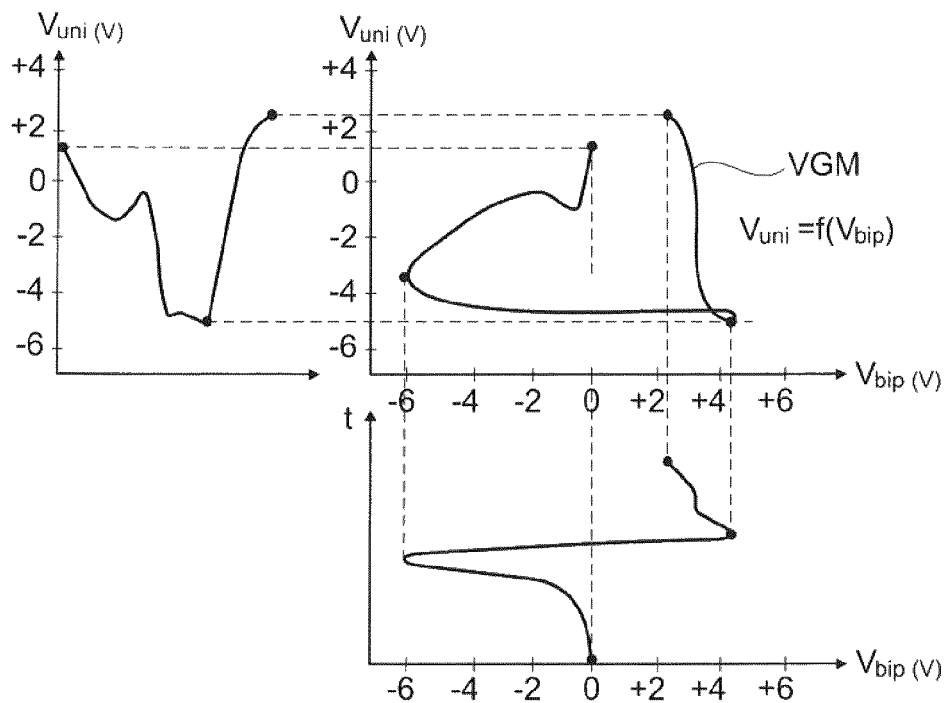
FIG. 5 illustrates the method to combine the unipolar and bipolar signals of FIG. 2 to obtain a vectogram 2D characteristic (VGM).

FIG. 5 shows the method to combine between them both $V_{bip}$ and $V_{uni}$ temporal components for a vectogram 2D characteristic (VGM) to reliably discriminate between cycles with and without anodal stimulation.

Referring still to FIG. 5, the $V_{uni}(t)$ and $V_{bip}(t)$ EGM signals are sampled and the successive collected samples of the two components thus collected are stored and combined to eliminate the temporal variable t and produce a parametric curve (the VGM characteristic) $V_{uni}=f(V_{bip})$. This curve $V_{uni}=f(V_{bip})$ is a parametric curve without temporal dimension (t is not a part of a voltage-voltage pair although t was used to match data points from the first voltage curve $V_{uni}$ and data points from the second voltage $V_{bip}$. The vectogram, in other words, can form a plot from the voltage amplitude variations of one of the temporal components ($V_{uni}$) versus the other ($V_{bip}$). The resulting set of voltage-voltage points forms a vectogram (VGM) representative of the cardiac cycle to be analyzed (or of a fraction of this cycle). In this application such a vectogram is sometimes referred to as a "non-temporal 2D characteristic." If graphically plotted, the VGM graphically has the form of a loop, time only appearing in the loop if evaluating the ordering of the pairs or the lines between the pairs.

Note incidentally that the "two dimensional" or "in two-dimension" (2D) analysis discussed here should not be construed as limiting the novelty of the invention to a two dimensional space. The invention may indeed apply to analysis in a higher multidimensional space (e.g., 3D or more wherein EGM signals from a single cavity are simultaneously collected on three or more channels).

Some embodiments can refrain from analyzing the entire cycle. Rather the analysis can include evaluating a significant fraction of this cycle (the one corresponding to the analysis window of width W). In such an embodiment, the representative curvilinear characteristic of the VGM is not a closed loop, since it is only a part of the complete cardiac cycle, namely, the QRS complex isolated inside the analysis window. The presence or absence of an anodal stimulation is detected by analyzing this VGM characteristic.

In one embodiment a morphological analysis of the of the vectogram is analyzed. Descriptor parameters of the vectogram are thus calculated and analyzed, which may include, for example, angles of the respective tangent vectors considered in various characteristic points of the VGM, the curvature of the VGM characteristic, or a combination of several parameters (e.g., a combination of the norm and of the angle of the tangent vectors). Different variants of these morphological analysis techniques used in other analysis algorithms are described in particular in EP 2368493 A1 above, which can be referred for further details.

In an exemplary embodiment that has some particular advantages, the VGM characteristic is examined only relative to a predetermined domain defined in the coordinate system in which it is plotted. For example, the VGM may be evaluated with respect to a rectangular domain of predefined size and position. The predefined size may be smaller than a vectogram associated with anodal capture. The rectangular domain may be used to conduct a topological analysis of the distribution of the VGM characteristic points relative to this domain. The position of these points inside or outside the predetermined domain may be the criterion used for deciding the presence or absence of an anodal stimulation.

Figures 6A, 6B:
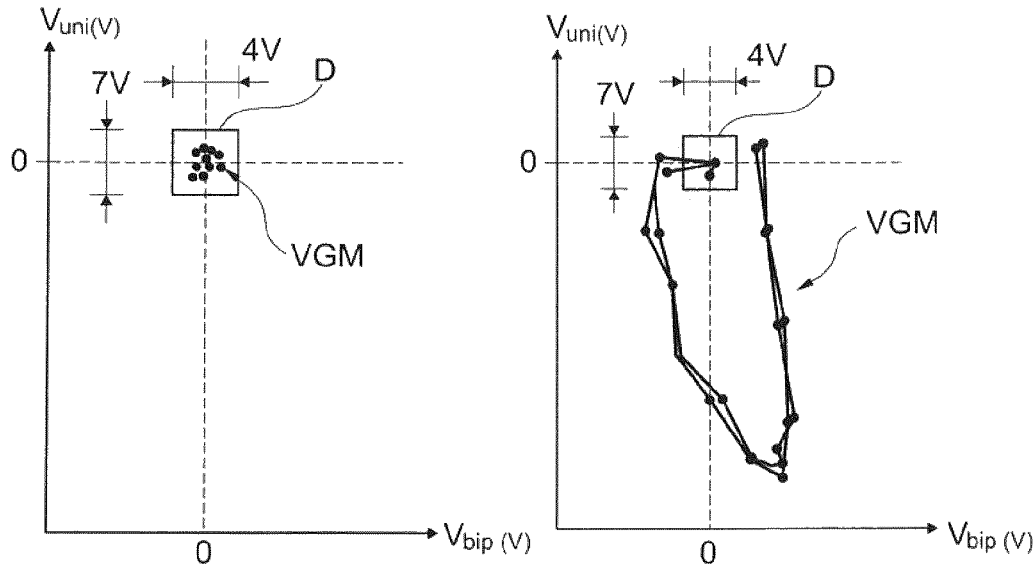
FIGS. 6a and 6b illustrate the vectograms respectively obtained with and without anodal stimulation, and the method to discriminate between these two situations by topological analysis of the vectogram.

More specifically, as shown in FIG. 6a, it can be seen that in case of no anodal stimulation, the VGM characteristic, determined by the successive sampling points of the $V_{bip}$ and $V_{uni}$ signals, simply consists of a cloud of points approximately around the point with coordinates {0,0}. However, in case of anodal stimulation, the VGM characteristic has the form of a curve which extends outside of domain D, as shown in FIG. 6b (an open curve if the sampling is only performed on a fraction of the cardiac cycle).

Thus, methods of the present application include defining a domain D in the space $\{V_{uni}, V_{bip}\}$ wherein the VGM characteristic is plotted. This domain D can be superimposed (in the case of graphical analysis) or otherwise compared relative to the VGM characteristic, to assess whether this VGM characteristic is or is not contained in the domain D, and to decide, depending on the case, the presence or absence of an anodal stimulation.

The domain D can be advantageously, as shown FIGS. 6a and 6b, a rectangular domain centered on the point of coordinates {0, 0}, of sides 4 V (for $V_{bip}$)×7 V (for $V_{uni}$). The decision criterion is for example the following:

If all the points of the VGM characteristic are inside this rectangle, then there is no anodal stimulation;

If at least one point of the characteristic is outside of the rectangle, then there is anodal stimulation.

Different criteria can be used, for example, requiring the presence of at least two points of the VGM characteristic outside the rectangle to decide the presence of an anodal stimulation, or even two consecutive points outside the rectangle. The domain D can be resized depending on the patient and/or the stimulation amplitude.

This method advantageously provides a simple and effective method to identify cycles with anodal stimulation, without implementing complex technical morphological analysis of the VGM characteristic, or comparison of this characteristic to reference models previously collected and requiring a regular update.

An exemplary embodiment may include adjusting the device to avoid capturing the result of spontaneous stimulation. To accomplish this, the method may include temporarily set the device with a short atrioventricular delay AVD during the capture test implementing the discrimination technique of the cycles with anodal stimulation of the invention.

The invention claimed is:

1. A method for use with an active medical device, comprising:
    delivering electrical stimulation pulses using electrodes adapted to be implanted in at least one heart chamber of a patient;
    collecting electrogram (EGM) signals representative of depolarization cardiac potentials; and
    detecting anodal stimulation by detecting a depolarization induced in a second cardiac chamber by a pacing delivered in a first heart chamber, wherein detecting anodal stimulation comprises:
    (i) delivering a stimulation pulse in the first cavity during at least one cardiac cycle;
    (ii) concurrently collecting, in the second cavity, at least two distinct EGM signals and deriving at least two respective distinct temporal components ($V_{bip}$, $V_{uni}$) from the two distinct EGM signals;
    (iii) combining the two temporal components to create a non-temporal two dimensional vectogram representative of the cardiac cycle to be analyzed, by pairing the temporal components $V_{uni}$ and $V_{bip}$; and (iv) determining the presence or absence of anodal stimulation by analyzing the non-temporal two dimensional vectogram.

2. The method of claim 1, further comprising:
deriving one of the temporal components ($V_{bip}$) from a bipolar near-field EGM signal collected between a bipolar distal electrode and a proximal electrode of the ventricular lead.

3. The method of claim 2, further comprising:
deriving the other of the temporal components ($V_{uni}$) from a unipolar far-field EGM signal collected between the distal electrode and a generator metal housing of the active implantable medical device.

4. The method of claim 1, further comprising:
determining the vectogram from the variations of the temporal components on a portion of the cardiac cycle to be analyzed, wherein the portion of the cardiac cycle to be analyzed is identified using an analysis temporal window, open at the delivery of the stimulation pulse in the first cavity.

5. The method of claim 4, further comprising:
temporarily shortening an atrioventricular delay of the device during the activation of the detection means of anodal stimulation, so that a spontaneous ventricular contraction occurring after an absence of collected ventricular depolarization is out of the analysis temporal window.

6. The method of claim 1, further comprising:
defining a predetermined domain in a reference frame corresponding to the space of the two temporal components; and
conducting a topological analysis to determine whether the vectogram is included or not in the domain.

7. The method of claim 6, further comprising:
outputting an indication of the absence of anodal stimulation when the vectogram is included within the predetermined domain;
outputting an indication of the presence of anodal stimulation when the vectogram is not included in the domain.

8. The method of claim 7, wherein the domain is a rectangular domain.

9. The method of claim 7, wherein the domain is centered on the point of origin of the point space for the two temporal components.

10. The method of claim 7, wherein the vectogram is described by a series of successive discrete points, and wherein the topological analysis compares the relative position of each point to the domain.

11. The method of claim 7, further comprising:
checking whether at least one point of the sampled vectogram is outside the domain, and determining that the vectogram is outside of the domain based on the one point.

12. The method of claim 7, further comprising:
checking whether at least two points of the vectogram are located outside the domain and determining that the vectogram is not included in the domain based on the two points being outside of the domain.

13. The method of claim 7, further comprising:
checking whether at least two consecutive points of the vectogram are outside the domain and determining that the vectogram is not included in the domain based on the two consecutive points being outside of the domain.

14. The method of claim 7, wherein vectograms are determined for a plurality of respective successive cardiac cycles; and wherein the topological analysis comprises checking whether at least one of the plurality of vectograms thus determined is outside the domain, then deciding the presence of anodal stimulation.

15. An active medical device, comprising:
a stimulation circuit delivering electrical stimulation pulses using electrodes adapted to be implanted in at least one heart chamber of a patient; and
at least one lead and a circuit configured to collect electrogram (EGM) signals representative of depolarization cardiac potentials;
wherein the circuit is configured to detect anodal stimulation by detecting a depolarization induced in a second cardiac chamber by a pacing delivered in a first heart chamber, wherein detecting anodal stimulation comprises:
(i) delivering a stimulation pulse in the first cavity during at least one cardiac cycle;
(ii) concurrently collecting, in the second cavity, at least two distinct EGM signals and to deriving at least two respective distinct temporal components ($V_{bip}$, $V_{uni}$) from the two distinct EGM signals;
(iii) combining the two temporal components to create a non-temporal two dimensional vectogram representative of the cardiac cycle to be analyzed, by pairing the temporal components $V_{uni}$ and $V_{bip}$; and
(iv) determining the presence or absence of anodal stimulation by analyzing the non-temporal two dimensional vectogram.

16. The active medical device of claim 15, wherein the circuit is further configured to derive one of the temporal components ($V_{bip}$) from a bipolar near-field EGM signal collected between a bipolar distal electrode and a proximal electrode of the ventricular lead.

17. The active medical device of claim 16, wherein the circuit is further configured to derive the other of the temporal components ($V_{uni}$) from a unipolar far-field EGM signal collected between the distal electrode and a generator metal housing of the active implantable medical device.

18. The active medical device of claim 17, wherein the circuit is configured to determine the vectogram from the variations of the temporal components on a portion of the cardiac cycle to be analyzed, wherein the portion of the cardiac cycle to be analyzed is identified using an analysis temporal window, open at the delivery of the stimulation pulse in the first cavity.

19. The active medical device of claim 18, wherein the circuit is further configured to:
define a predetermined domain in a reference frame corresponding to the space of the two temporal components; and
conduct a topological analysis to determine whether the vectogram is included or not in the domain.

20. The active medical device of claim 19, wherein the circuit is further configured to:
generate an indication of the absence of anodal stimulation when the vectogram is included within the predetermined domain; and wherein the circuit is further configured to generate an indication of the presence of anodal stimulation when the vectogram is not included in the domain.

21. The active medical device of claim 20, wherein the domain is a rectangular domain and wherein the domain is centered on the point of origin of the point space for the two temporal components.

* * * * *